(12) United States Patent
Dyke et al.

(10) Patent No.: US 6,455,561 B1
(45) Date of Patent: Sep. 24, 2002

(54) HETEROCYCLIC COMPOUNDS AND THEIR THERAPEUTIC USE

(75) Inventors: Hazel Joan Dyke; Christopher Lowe; John Gary Montana, all of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/976,811

(22) Filed: Oct. 12, 2001

Related U.S. Application Data

(63) Continuation of application No. 09/780,657, filed on Feb. 9, 2001, now Pat. No. 6,331,556.

(30) Foreign Application Priority Data

Feb. 11, 2000 (GB) .............................. 0003257

(51) Int. Cl.$^7$ ..................... A61K 31/42; A61K 31/415; A61K 31/4164; C07D 261/06; C07D 413/12

(52) U.S. Cl. .................... 514/380; 548/245; 548/311.4; 548/364.4

(58) Field of Search .............................. 548/245, 311.4, 548/364.4; 514/380, 397, 407

(56) References Cited

U.S. PATENT DOCUMENTS

| 5,925,636 A | 7/1999 | Dyke et al. |
| 5,972,936 A | 10/1999 | Dyke et al. |
| 6,121,274 A | 9/2000 | Ulrich et al. |

FOREIGN PATENT DOCUMENTS

| WO | 9603399 | 2/1996 |
| WO | 9744337 | 11/1997 |
| WO | 9807715 | 2/1998 |
| WO | 9940085 | 8/1999 |

OTHER PUBLICATIONS

McGarry, D.G. et al. (1999) "Benzofuran Based PDE4 Inhibitors" *Bioorganic & Medicinal Chemistry* 7:1131–1139.

Primary Examiner—Joseph K. McKane
Assistant Examiner—Golam M. M. Shameem
(74) Attorney, Agent, or Firm—Saliwanchik, Lloyd & Saliwanchik

(57) ABSTRACT

The present invention pertains to compositions and methods for treating disease states which are capable of being modulated by inhibition of phosphodiesterase IV or Tumour Necrosis Factor, or that is a pathological condition associated with a function of phosphodiesterase IV, eosinophil accumulation or a function of the eosinophil, said method comprising administering to a person or animal in need of such treatment an effective amount of the compound of a formula

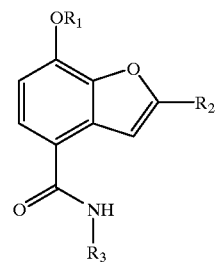

wherein $R_1$ is $C_{1-3}$ alkyl optionally substituted with one or more fluorines;

$R_2$ is $CH_2OCH_3$ or 2 or 3-tetrahydrofuranyl;

$R_3$ is a pyrazole, imidazole or isoxazole group of partial formula (A), (B) or (C)

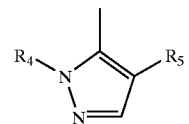

(A)

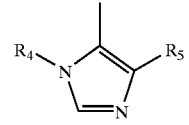

(B)

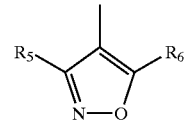

(C)

$R_4$ is $C_{1-3}$ alkyl; and $R_5$ and $R_6$, which may be the same or different, each represents $C_{1-3}$ alkyl, halogen, $CF_3$ or CN;

or a pharmaceutically-acceptable salt thereof

8 Claims, No Drawings

HETEROCYCLIC COMPOUNDS AND THEIR THERAPEUTIC USE

CROSS-REFERENCE TO RELATED APPLICATION

This application is a continuation of U.S. application Ser. No. 09/780,657, filed Feb. 9, 2001, now U.S. Pat. No. 6,331,556.

FIELD OF THE INVENTION

The present invention relates to novel heterocyclic compounds and to their formulation and use as pharmaceuticals.

BACKGROUND OF THE INVENTION

The modes of action of phosphodiesterases and also tumour necrosis factor (TNF), and the therapeutic utilities of inhibitors thereof, are described in WO-A-97/4433 7 and U.S. Pat. Nos. 5,925,636 and 5,972,936, the contents of which are incorporated herein by reference. These reference describe benzofurans having such activity.

SUMMARY OF THE INVENTION

This invention provides novel compounds having therapeutic utility, in particular for the treatment of disease states associated with proteins which mediate cellular activity, for example by inhibiting TNF and/or PDE IV. According to the invention, the compounds are of formula (i):

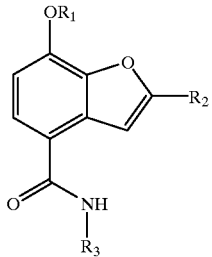

wherein $R_1$ is $C_{1-3}$ alkyl optionally substituted with one or more fluorines;

$R_2$ is $CH_2OCH_3$ or 2 or 3-tetrahydrofuranyl, $R_3$ is a pyrazole, imidazole or isoxazole group of partial formula (A), (B) or (C)

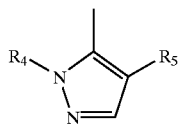

(A)

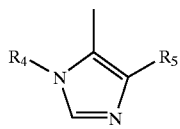

(B)

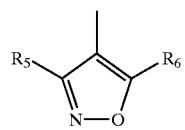

(C)

$R_4$ is $C_{1-3}$ alkyl and $R_5$ and $R_6$, which may be the same or different, each represents $C_{1-3}$ alkyl, halogen, $CF_3$ or CN or a pharmaceutically-acceptable salt thereof In summary, the compounds of the invention represent a selection within the scope of WO-A-97/44337. The novel compounds have superior in vivo activity.

This invention provides also a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof

DESCRIPTION OF THE INVENTION

The term "$C_{1-3}$ alkyl" means methyl, ethyl, propyl or isopropyl.

One group of compounds of the invention is of formula (i) in which $R_1$ is $CH_3$ or $CHF_2$.

$R_3$ may in particular be a pyrazole of partial formula (A) or an isoxazole of partial formula (C). When $R_3$ is a pyrazole moiety, $R_4$ is especially $CH_3$ and $R_5$ is particularly CN, $CH_3$, Cl or $CF_3$. Where $R_3$ is an isoxazole moiety, $R_5$ is especially $CH_3$, $CF_3$ or CN and $R_6$ is particularly $CH_3$, $CF_3$ or CN.

The compounds of the Examples are especially preferred.

It will be appreciated by those skilled in the art that compounds of formula (i) in which $R_2$ represents tetrahydrofuran contain a chiral centre. This invention extends to both enantiomers and all mixtures thereof, including racemic mixtures.

Certain of the compounds of formula (i) which contain a basic group form acid addition salts. Suitable acid addition salts include pharmaceutically-acceptable inorganic salts such as the sulphate, nitrate, phosphate, borate, hydrochloride and hydrobromide, and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

Compounds of the invention may be prepared by reaction of an appropriate carboxylic acid of formula (ii) with a suitable amine of formula (iii) as described in WO 97/44337. Carboxylic acids of formula (ii) may be conveniently prepared from compounds of formula (iv) by bromination followed by palladium-catalysed carbonylation as described in WO 97/44337. Amines of formula (iii) are either commercially available, previously described compounds, or are prepared using standard conditions known to those skilled in the art.

Compounds of formula (iv) in which $R_1$ represents methyl and $R_2$ represents $CH_2OCH_3$ may be conveniently prepared from o-Vanillin as shown below. o-Vanillin is treated with bromoacetaldehyde dimethyl acetal in the presence of a base, such as potassium carbonate, in a suitable solvent such as N,N-dimethylformamide, favourably at elevated temperature. The resultant acetal can then be cyclised, for example by heating in acetic acid, to provide 7-methoxybenzofuran-2-carbaldehyde. The aldehyde may be reduced using any suitable reducing agent known to those skilled in the art, such as sodium borohydride. The resultant alcohol may be methylated using any appropriate methylating agent, such as methyl iodide, in the presence of an appropriate base, such as sodium hydride.

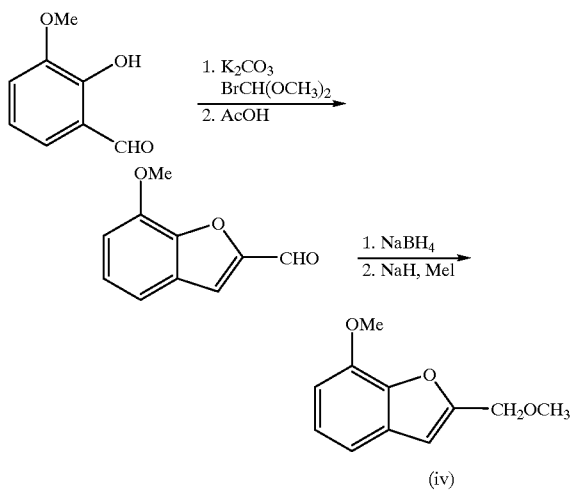

Compounds of formula (iv) in which $R_1$ represents methyl and $R_2$ represents 3-tetrahydrofuranyl may be prepared from 7-methoxybenzofuran as depicted below. 7-Methoxybenzofuran may be deprotonated by treatment with any suitable base, such as butyllithium, and the resultant anion added to tetrahydrofuran-3-one. The resultant alcohol may be converted to a leaving group, such as a mesylate, and then eliminated. The alkene thus formed may be reduced using any suitable reducing agent, such as Raney nickel and hydrogen.

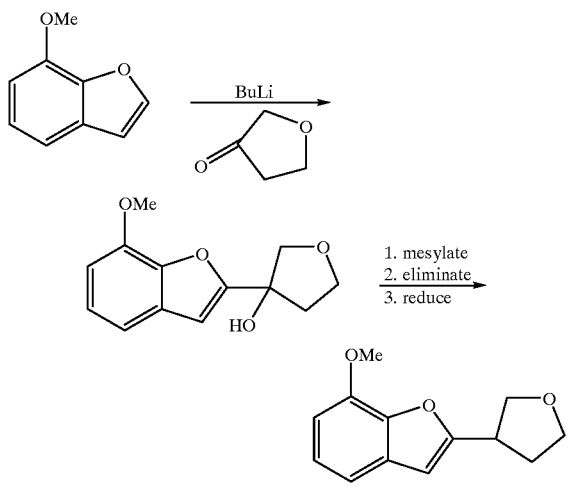

Compounds of formula (iv) in which $R_1$ represents methyl and $R_2$ represents 2-tetrahydrofaranyl may be prepared from 7-methoxybenzofuran-2-carbaldehyde as shown below. A suitably protected Grignard reagent derived from 1,3-propanediol may be added to 7-methoxybenzofuran-2-carbaldehyde, and the protecting group may then be removed. A suitable protecting group may be tert-butyldimethylsilyl, which may be removed using any standard conditions known to those skilled in the art, for example tetrabutylammonium fluoride. Cyclisation of the resultant diol may be achieved using any appropriate conditions, such as p-toluenesulphonic acid and molecular sieves in a suitable solvent such as dicloromethane.

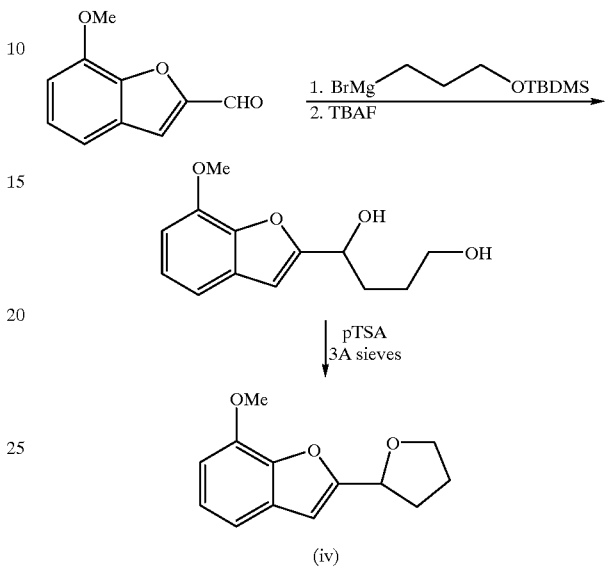

Compounds of formula (iv) in which $R_1$ represents difluoromethoxy may be prepared by demethylation, and subsequent difluoromethylation, of suitable intermediates in which $R_1$ represents methyl. Such demethylation may be carried out using any suitable conditions known to those skilled in the art. Suitable conditions include the use of ethane thiolate in an appropriate solvent, such as N,N-dimethylformamide, at a suitable temperature. Suitable temperatures include elevated temperatures, favourably 140° C. Difluoromethylation of the resultant phenols may be carried out using any suitable conditions known to those skilled in the art. Suitable conditions include the use of chlorodifluoromethane and a suitable base in an appropriate solvent at an appropriate temperature. Favourably, the reaction is conducted in dioxane as solvent using aqueous sodium hydroxide as base. Elevated temperatures, such as reflux temperature, may be employed.

The invention includes the prevention and treatment of TNF-mediated disease or disease states, by which is meant any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biological responses and binds to the same cellular receptor, both TNF-α and TNF-β are inhibited by compounds of the present invention and thus are herein referred to collectively as "TNF" unless specifically delineated otherwise.

PDE IV inhibitors are useful in the treatment of a variety of allergic and inflammatory diseases, including: asthma, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (i) are preferably in pharmaceutically-acceptable form. By pharmaceutically-acceptable form is meant, inter alia, a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%. When used herein the term "pharmaceutically-acceptable" encompasses materials suitable for both human and veterinary use.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose. Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically-acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 μm, such as from 0.1 to 50 μm, preferably less than 10 μm, for example from 1 to 10 μm, 1 to 5 μm or from 2 to 5 μm. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions, the compound can be dissolved in water for injection and filter-sterilised before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically-acceptable salt thereof, will compromise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0. 1 to 1000 mg, such as 0. 5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04,0.05, 0.06, 0.08, 0.1 or 0.2 mg/kg/day, and such therapy may extend for a number of weeks or months.

Assay Methods

The assays used to confirm the phosphodiesterase IV inhibitory activity of compounds of formula (I) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV related disease states in those assays.

The ability of compounds of formula (i) to inhibit TNF production in human peripheral blood mononuclear cells (PMBC's) is measured as follows. PMBC's are prepared from freshly taken blood or "Buffy coats" by standard procedures. Cells are plated out in RPMI1640 +1% foetal calf serum in the presence and absence of inhibitors. LPS (Lipopolysaccharide (endotoxin); 100 ng/ml) is added and cultures are incubated for 22 h at 37° C. in an atmosphere of 95% air/5% $CO_2$. Supernatants are tested for TNFα by ELISA (Enzyme linked immunosorbent assay) using commercially available kits.

Activity in a guinea pig lung model is measured using the procedures described by Mauser et al, Am. Rev. Respir. Dis. 148:1623 (1993), and Am. J. Respir. Crit. Care Med. 152:467 (1995).

The compound of Example 2 of WO-A-97/44337 exhibits 41% inhibition of eosinophilia in the guinea pig model when dosed at 30 mg/kg. Example 10 herein (representative of the present invention) achieves 35% inhibition when dosed at 3 mg/kg.

The following Examples illustrate the invention.

Intermediate 1

2-(2-Formyl-6-methoxyphenoxy)acetaldehyde, dimethyl acetal o-Vanillin (20 g) and potassium carbonate (18 g) were stirred in N, N-dimethylformamide (80 ml) at room temperature for 30 minutes. Bromoacetaldehyde dimethyl acetal (24 g) was added dropwise ensuring that the temperature did not rise above 50° C. The mixture was then heated at reflux for 4 hours then cooled to room temperature. Diethyl ether (30 ml) was added and the mixture was filtered. The solid was washed with ether (2×30 ml) and the combined organic phases were concentrated in vacuo to give the title compound (33 g) as a green oil.

TLC $R_f$ 0. 66 (50% ethyl acetate in hexane).

Intermediate 2

7-Methoxybenzofuran-2-carbaldehyde 2-(2-Formyl-6-methoxyphenoxy)acetaldehyde, dimethyl acetal (31 g) was heated to reflux in glacial acetic acid (120 ml) overnight. The mixture was then cooled and the solvent removed in vacuo to give a red oil. Purification by Kugelrohr distillation gave the title compound (17 g) as a pale yellow oil which solidified on standing.

TLC $R_f$ 0.71 (dichloromethane).

Intermediate 3

7-Methoxybenzofuran-2-yl-methanol

Sodium borohydride (0.462 g) was added in one portion to a stirred solution of 7-methoxybenzofuran-2- carbaldehyde (2.15 g) in methanol (50 ml) at room temperature and the reaction was stirred for 3 hours. The reaction mixture was then diluted with water (100 ml) and extracted with dichloromethane (3×30 ml). The organic extracts were combined, washed with water (30 ml), dried over magnesium sulphate, filtered and the solvent removed in vacuo to afford the title compound (2.10 g) as a pale orange liquid. TLC $R_f$ 0.51 (2% methanol in dichloromethane).

Intermediate 4

7-Methoxy-2-methoxy-methylbenzofuran

Sodium hydride (3.82 g, 60% in mineral oil) was added to a solution of 7-methoxy-benzofuran-2-ylmethanol (11.21 g) in dry tetrahydrofuran (300 ml) under an atmosphere of dry nitrogen at room temperature. After 10 minutes iodomethane (15.67 ml) was added and the reaction was left to stir overnight. The solvent was removed in vacuo and the residue partitioned between ethyl acetate (100 ml) and water (50 ml). The organic extract was washed with water (50 ml), followed by brine (50 ml), dried over magnesium sulphate, filtered and the solvent removed in vacuo to afford the title compound (13.32 g) as a yellow oil.
TLC $R_f$ 0.70 (50% ethyl acetate in hexane).

Intermediate 5

4-(tert-Butyldimethylsilanyloxy)-1-(7-methoxybenzofuran-2-yl)-butan-1-ol

A suspension of dried magnesium turnings (0.42 g) in anhydrous tetrahydrofuran (20 ml) was treated with 2 ml of (3-Bromopropoxy)-tert-butyldimethylsilane (4.4 g) in anhydrous tetrahydrofuran (10 ml) at room temperature under a dry nitrogen atmosphere. Initiation was achieved by the addition of catalytic iodine and warming to 80° C. The remaining solution (8 ml) was then added carefully. The reaction was cooled to −5° C. and a solution of 7-methoxybenzofuran-2-carbaldehyde (3 g) in anhydrous tetrahydrofuran (20 ml) was added carefully. After stirring at ambient temperature overnight the solvent was removed in vacuo. The residue was partitioned between ethyl acetate (100 ml) and saturated aqueous ammonium chloride solution (100 ml). The organic extract was dried over magnesium sulphate, filtered and preadsorbed onto silica. Purification by column chromatography on silica eluting with 10% ethyl acetate in hexane afforded the title compound as a yellow oil (4.88 g).
TLC $R_f$ 0.75 (20% ethyl acetate).

Intermediate 6

1-(7-Methoxybenzofuran-2-yl)-butane-1,4-diol

Tetrabutylammonium fluoride (12 ml,1M in tetrahydrofuran) was added to a stirred solution of 4-(tert-butyldimethylsilanyloxy)-1-(7-methoxybenzofuran-2-yl)-butan-1-ol (4 g) in tetrahdrofuran (50 ml) at 0° C. After stirring cooled for 2 hours the reaction was warmed to room temperature and allowed to stir for a further 1 hour. The solvent was removed in vacuo and the residue partitioned between ethyl acetate (100 ml) and water (50 ml). The organic extract was dried over magnesium sulphate, filtered and preadsorbed onto silica. Purification by column chromatography on silica eluting with ethyl acetate yielded the title compound as a tan oil (2.34 g).
TLC $R_f$ 0.15 (50% ethyl acetate in hexane).

Intermediate 7

7-Methoxy-2-(tetrahydrofuran-2-yl)-benzofuran

A solution of 1-(7-methoxybenzofuran-2-yl)-butane-1,4-diol (0.88 g) was treated with p-toluenesulfonic acid monohydrate (10 mg) and 3 Å molecular sieves in dichloromethane (10 ml) at ambient temperature. After stirring for 1 hour the solvent was removed in vacuo. The residue was purified by column chromatography on silica eluting with 20% ethyl acetate in hexane to give the title compound as a yellow oil (0.58 g).
TLC $R_f$ 0.35 (20% ethyl acetate in hexane).

Intermediate 8

3-(7-Methoxybenzofuran-2-yl)-tetrahydrofuran-3-ol

Methyl sulfoxide (1.16 ml) was added dropwise to a stirred solution of oxalyl chloride (0.71 ml) in dry dichloromethane (15 ml) at −60° C. under an inert atmosphere. After stirring at this temperature for 30 minutes a solution of 3-hydroxytetrahydrofuran (0.55 ml) in dry dichloromethane was added carefully. After a further 30 minutes triethylamine was added dropwise and the reaction allowed to warm to room temperature. The reaction was poured onto water (40 ml) and extracted with dichloromethane (30 ml). The organic phase was washed with water (50 ml), brine (2×50 ml) and saturated aqueous sodium hydrogen carbonate solution (2×50 ml). After drying over magnesium sulphate the solvent was removed in vacuo to afford tetrahydro-furan-3-one as a yellow gum (0.19 g). n-Butyllithium (0.72 ml, 1.6M in hexanes) was added dropwise to a stirred solution of 7-methoxybenzofuran (0.15 g) in dry tetrahydrofuran (5 ml) at −78° C. under a dry nitrogen atmosphere. After stirring for 20 minutes a solution of tetrahydrofuran-3-one (90 mg) in dry tetrahydrofuran (2 ml) was added carefully. After stirring for a further 15 minutes at −78° C. the reaction was allowed to warm to room temperature. The reaction was carefully quenched with water and the solvent removed in vacuo. The residue was partitioned between ethyl acetate (2×15 ml) and water (15 ml). The combined organic extracts were dried over magnesium sulphate, filtered and concentrated in vacuo. The residue was purified by column chromatography on silica eluting with 50% ethyl acetate in hexane to give the title compound as an orange gum (64 mg).
TLC $R_f$ 0.37 (50% ethyl acetate in hexane).

Intermediate 9

7-Methoxy-2-(tetrahydrofuran-3-yl)-benzofuran

Triethylamine (0.19 ml) was added to a stirred solution of 3-(7-methoxybenzofuran-2-yl)-tetrahydrofuran-3-ol (0.15 g) in dry dichloromethane (8 ml) at room temperature under a dry nitrogen atmosphere. Methanesulfonyl chloride (0.08 ml) was then added followed by a catalytic amount of 4-(dimethylamino)pyridine. After stirring at room temperature overnight the solvent was removed in vacuo. The residue was purified by column chromatography on silica eluting with 50% ethyl acetate in hexane to give a mixture of 2-(4,5-dihydrofuran-3-yl)-7-methoxybenzofuran and 2-(2,5-dihydrofuran-3-yl)-7-methoxybenzofuran (85 mg) as a yellow solid.

A solution of the alkene mixture (85 mg) in ethanol (10 ml) was treated with Raney Nickel and hydrogenated at atmospheric pressure for 1 hour. The reaction mixture was filtered through celite and the solvent was removed in vacuo to give the title compound as a white solid (80 mg).
TLC $R_f$ 0.49 (33% ethyl acetate in hexane).

Intermediate 10

2-(Tetrahydrofuran-3-yl)-benzofuran-7-ol

Sodium hydride (0. 19 g, 60% in mineral oil) was added to a stirred solution of ethane thiol (0.34 ml) in N, N-dimethylformamide (6 ml) at room temperature under a dry nitrogen atmosphere. After stirring for 15 minutes 7-methoxy-2-(tetrahydrofuran-3-yl)-benzofuran (0.5 g) in N,N-dimethylformamide (6 ml) was added and the reaction heated to 140° C. for 2 hours. After cooling to room temperature the solvent was removed in vacuo. The residue was partitioned between ethyl acetate (50 ml) and water (50 ml). The organic extract was dried over magnesium sulphate, filtered and preadsorbed onto silica. Purification by column chromatography on silica eluting with 50% ethyl acetate in heptane afforded the title compound as a brown oil (0.37 g).
TLC $R_f$ 0.38 (50% ethyl acetate in heptane).

Intermediate 11 tert-Butyldimethyl-[2-(tetrahydrofuran-3-yl)-benzofuran-7-yloxy]-silane

Sodium hydride (80 mg, 60% dispersion in mineral oil) was added to a stirred solution of 2-(tetrahydrofuran-3-yl)-benzofuran-7-ol (0.37 g) in dry tetrahydrofuran (10 ml) at room temperature under a dry nitrogen atmosphere. After stirring for 10 minutes tert-butyldimethylsilyl chloride (0.27 g) was added and the reaction stirred for 90 minutes. The reaction mixture was partitioned between ethyl acetate (30 ml) and water (2×25 ml). The combined aqueous washings were extracted with ethyl acetate (30 ml). The organic extracts were combined, dried over magnesium sulphate, filtered and concentrated in vacuo to give the title compound as a yellow oil (0.58 g).
TLC $R_f$ 0.7 (50% ethyl acetate in heptane).

Intermediate 12

4-Bromo-7-methoxy-2-methoxymethylbenzofuran

A solution of 7-methoxy-2-methoxymethylbenzofuran (13.32 g) in acetonitrile (500 ml) was stirred at room temperature. N-bromosuccinimide (11.04 g) was added and stirring continued for 2 days after which the solvent was removed in vacuo. The resulting oil was partitioned between ethyl acetate (100 ml) and sodium metasulfite solution (50 ml), the organic extract washed with more sodium metasulfite solution (2×50 ml), followed by brine (50 ml). The organic layer was separated, dried over magnesium sulphate, filtered and the solvent removed in vacuo to afford the title compound as a yellow oil (18.61 g).
TLC $R_f$ 0.73 (50% ethyl acetate in hexane).
The following compounds were prepared in a similar manner.

Intermediate 13

4-Bromo-7-methoxy-2-(tetrahydrofuran-2-yl)-benzofuran

Starting from 7-methoxy-2-(tetrahydrofuran-2-yl)-benzofuran (0.58 g). The title compound was obtained as a yellow oil (0.8 g).
TLC $R_f$ 0.35 (20% ethyl acetate in hexane).

Intermediate 14

4-Bromo-7-methoxy-2-(tetrahydrofuran-3-yl)-benzofuran

Starting from 7-methoxy-2-(tetrahydrofuran-3-yl)-benzofuran (80 mg). The title compound was obtained as a brown oil (65 mg).
TLC $R_f$ 0.46 (33% ethyl acetate in hexane).

Intermediate 15

[4-Bromo-2-(tetrahydrofuran-3-yl)-benzofuran-7-yloxy]-tert-butyldimethylsilane

Starting from tert-Butyldimethyl-[2-(tetrahydrofuran-3-yl)-benzofuran-7-yloxy]-silane (0.59 g). Purification by column chromatography on silica eluting with 20% ethyl acetate in heptane afforded the title compound as a brown oil (0.31 g).
TLC $R_f$ 0.48 (20% ethyl acetate in heptane).

Intermediate 16

4-Bromo-2-(tetrahydrofuran-3-yl)-benzofuran-7-ol

Tetrabutylammonium fluoride (8.1 ml, 1M in tetrahydrofuran) was added to a stirred solution of [4-bromo-2-(tetrahydrofuran-3-yl)-benzofuran-7-yloxy]-tert-butyldimethylsilane (2.69 g) in dry tetrahydrofuran (80 ml) at 0° C. under a dry nitrogen atmosphere. After stirring at this temperature for 45 minutes the solvent was removed in vacuo. The residue was partitioned between ethyl acetate (75 ml) and water (75 ml). The organic extract was dried over magnesium sulphate, filtered and concentrated in vacuo. Purification by column chromatography on silica eluting with 50% ethyl acetate in heptane afforded the title compound as a clear oil (1 g).
TLC $R_f$ 0.39 (50% ethyl acetate in heptane).

Intermediate 17

4-Bromo-2-methoxymethylbenzofuran-7-ol

To a stirred solution of sodium hydride (334 mg, 60% in mineral oil) in dry N, N-dimethylformamide (25 ml) under an atmosphere of dry nitrogen at room temperature was added dropwise ethane thiol (0.586 ml). After stirring for 20 minutes a solution of 4-bromo-7-methoxy-2-methoxymethylbenzofuran (2.04 g) in N,N-dimethylformamide (7 ml) was added dropwise and the reaction mixture was heated at 160° C. for 2 hours. The reaction was cooled and the solvent removed in vacuo. The residue was dissolved in ethyl acetate (70 ml) and washed with ammonium chloride solution (70 ml). The organic extract was dried over magnesium sulphate, filtered and the solvent removed in vacuo. Purification by column chromatography on silica eluting with 50% ethyl acetate in hexane afforded the title compound as a white solid (1.21 g).
TLC $R_f$ 0.65 (50% ethyl acetate in hexane).

Intermediate 18

4-Bromo-7-difluoromethoxy-2-methoxymethylbenzofuran

To a solution of 4-bromo-2-methoxymethylbenzofuran-7-ol in 1,4-dioxane (25 ml) heated to 100° C. was added dropwise a solution of sodium hydroxide (0.76 g) in water (2ml). Chlorodifluoromethane was bubbled through the reaction mixture for 2 hours after which it was allowed to cool to room temperature and the organic solvent removed in vacuo. The resulting aqueous slurry was extracted with ethyl acetate (3×25 ml). The organic extracts were dried over magnesium sulphate, filtered and the solvent removed in vacuo. Purification by column chromatography on silica eluting with 20% ethyl acetate in hexane afforded the title compound as an off-white solid (1.24 g).
TLC $R_f$ 0.73 (20% ethyl acetate in hexane).

The following compound was prepared in a similar manner.

Intermediate 19

4-Bromo-7-difluoromethoxy-2-(tetrahydrofuran-3-yl)-benzofuran

Starting from 4-bromo-2-(tetrahydrofuran-3-yl)-benzofuran-7-ol (1 g). Purification by column chromatography on silica eluting with 30% ethyl acetate in heptane gave the title compound as a pale yellow solid (0.8 g).
TLC $R_f$ 0.64 (50% ethyl acetate in heptane).

Intermediate 20

7-Methoxy-2-methyoxymethylbenzofuran-4-carboxylic Acid

4-Bromo-7-methoxy-2-methoxymethylbenzofuran (18.61 g), Pplladuim chloride (3.09 g), bis-diphenylphosphinopropane (6.60 g), triethylamine (49.65 ml), tetrahydrofuran (200 ml), and water (50 ml) were combined in a Parr pressure reactor. The vessel was purged with carbon monoxide 3 times before being charged with carbon monoxide at 140 psi. The vessel was then heated at 90° C. for 3 days before cooling and release of the pressure. The reaction mixture was concentrated in vacuo and the residue taken up in 2N sodium hydroxide solution (250 ml). The reaction mixture was washed with ethyl acetate (2×300 ml) and then the aqueous layer was acidified to pH 5 with 10N hydrochloric acid. The resulting mixture was extracted with dicloromethane (2×100 ml), the combined organic extracts dried over magnesium sulphate, filtered and the solvent removed in vacuo to afford the title compound as a yellow solid (14.24 g).
TLC $R_f$ 0.31 (50% ethyl acetate in hexane).

The following compounds were prepared in a similar manner.

Intermediate 21

7-Difluoromethoxy-2-methoxymethylbenzofuran-4-carboxylic Acid

Starting from 4-bromo-7-difluoromethoxy-2-methoxymethylbenzofuran (1.24 g).

After carbonylation the reaction mixture was concentrated in vacuo to remove organic solvent and the subsequent aqueous residue extracted with dichloromethane (50mil). The aqueous layer was acidified to pH4 with glacial acetic acid and extracted with ethyl acetate (2×100 ml). The combined organic extracts were dried over magnesium sulphate, filtered and the solvent removed in vacuo to afford the title compound as a white solid.
TLC $R_f$ 0.63 (50% ethyl acetate in hexane).

Intermediate 22

7-Methoxy-2-(tetrahydrofuran-3-yl)-benzofuran-4-carboxylic Acid

Starting from 4-bromo-7-methoxy-2-(tetrahydrofuran-3-yl)-benzofuran (1.9 g). The title compound was obtained as an orange solid (1.18 g).
TLC $R_f$ 0.58 (ethyl acetate).

Intermediate 23

7-Difluoromethoxy-2-(tetrahydrofuran-3-yl)-benzofuran-4-carboxylic Acid

Starting from 4-bromo-7-difluoromethoxy-2-(tetrahydrofuran-3-yl)-benzofuran (0.8 g). The title compound was obtained as a cream solid (0.72 g).
TLC $R_f$ 0.24 (50% ethyl acetate in heptane).

Intermediate 24

7-Methoxy-2-(tetrahydrofuran-2-yl)-benzofuran-4-carboxylic Acid

Starting from 4-bromo-7-methoxy-2-(tetrahydrofuran-2-yl)-benzofuran (0.8 g). The title compound was obtained as an off white solid (0.63 g).
TLC $R_f$ 0.13 (20% ethyl acetate in hexane).

Intermediate 25

7-Methoxy-2-methoxymethylbenzofuran-4-carboyxlic Acid 4-nitrophenyl Ester

7-Methoxy-2-methyoxymethylbenzofuran-4-carboxylic acid (0. 42 g),p-nitrophenol (0.29 g), 1-(3-dimethylaminopropyl)-3-ethylcarbodiimide hydrochloride (0.4 g) and 4-dimethylaminopyridine (catalytic) in dry dichloromethane (30 ml) were stirred overnight at room temperature. The reaction mixture was washed with water (40 ml) and the aqueous layer extracted with dichloromethane (40 ml). The organic extracts were combined, washed with water (80 ml), dried over magnesium sulphate, filtered and the solvent removed in vacuo. The residue was triturated with ethyl acetate and diethyl ether to afford the title compound as a cream solid (0.42 g).
TLC $R_f$ 0.61 (50% ethyl acetate in hexane).

The following compounds were prepared in a similar manner.

Intermediate 26

7-Difluoromethoxy-2-methoxymethylbenzofuran-4-carboxylic Acid 4-nitrophenyl Ester Starting from 7-difluoromethoxy-2-methoxymethylbenzofuran-4-carboxylic acid (118 mg). Purification by trituration with diethyl ether afforded the title compound as a pale yellow solid (83 mg).
TLC $R_f$ 0.54 (50% ethyl acetate in heptane).

Intermediate 27

7-Methoxy-2-(tetrahydrofuran-3-yl)-benzofuran-4-carboxylic Acid 4-nitrophenyl Ester Starting from 7-methoxy-2-(tetrahydrofuran-3-yl)-benzofuran-4-carboxylic acid (1.16 g). The title compound was obtained as a brown solid (1.76 g).
TLC $R_f$ 0.82 (5% methanol in dichloromethane).

Intermediate 28

7-Difluoromethoxy-2-(tetrahydrofuran-3-yl)-benzofuran-4-carboxylic Acid 4-nitrophenyl Ester Starting from 7-difluoromethoxy-2-(tetrahydrofuran-3-yl)-benzofuran-4-carboxylic acid (0.3 g). Purification by column chromatography on silica eluting with 50% ethyl acetate in heptane gave the title compound as a white solid (0.38 g).
TLC $R_f$ 0.55 (50% ethyl acetate in heptane).

Intermediate 29

7-Methoxy-2-(tetrahydrofuran-2-yl)-benzofuran-4-carboxylic Acid 4-nitrophenyl Ester Starting from 7-methoxy-2-(tetrahydrofuran-2-yl)-benzofuran-4-carboxylic acid (0.3 g). Purification by column chromatography on silica eluting with 50% ethyl acetate in heptane gave the title compound as a cream solid (0.37 g).
TLC $R_f$ 0.48 (50% ethyl acetate in heptane).

Intermediate 30

4-Chloro-2-methyl-2H-pyrazol-3-ylamine

To a solution of 2-methyl-2H-pyrazol-3-ylamine (0.30 g) in conc. hydrochloric acid (4 ml) heated to 85° C. was added dropwise hydrogen peroxide (0.67 ml of a 30% solution in water). Heating continued for 60 mins. After cooling to 0° C. the solution was taken to pH 11 using 46/48% w/w sodium hydroxide solution. The solid formed was filtered off and the filtrate extracted with ethyl acetate (4×50 ml). The combined organic layers were dried over magnesium sulphate, filtered and concentrated in vacuo. The resulting product was combined with the previously collected product to afford the title compound as a brown solid (0.13 g).
TLC $R_f$ 0.50 (10% methanol in dichloromethane).

EXAMPLE 1

7-Methoxy-2-(tetrahydrofuran-3-yl)-benzofuran-4-carboxylic Acid (3,5-dimethylisoxazol-4-yl)-amide To a stirred solution of 3,5-dimethylisoxazol-4-ylamine (88 mg) in N,N-dimethylformamide (7 ml) under an atmosphere of dry nitrogen at room temperature was added sodium bis(trimethylsilyl)amide (0.78 ml, 1.0 M solution in tetrahydrofuran). The reaction was stirred for 5 minutes. 7-Methoxy-2-(tetrahydro-furan-3-yl)-benzofuran-4-carboxylic acid 4-nitrophenyl ester (200 mg) was then added and stirring continued for 15 minutes. Water (1 ml) was added and the solvent was removed in vacuo. The resulting residue was purified by column chromatography on silica eluting with 50% ethyl acetate in heptane followed by trituration with diethyl ether affording the title compound as a cream solid (52 mg).
TLC $R_f$ 0.60 (50% ethyl acetate in heptane).
Mp 183.5–185.2° C.

The following compounds were prepared in a similar manner.

EXAMPLE 2

7-Difluoromethoxy-2-(tetrahydrofuran-3-yl)-benzofuran-4-carboxylic Acid (4-cyano-2-methyl-2-H-pyrazol-3-yl)-amide Prepared from 7-difluoromethoxy-2-(tetrahydrofuran-3-yl)-benzofuran-4-carboxylic acid 4-nitrophenyl ester (380 mg) and 5-amino-1-methyl-1-H-pyrazole-4-carbonitrile (220 mg). The reaction was stirred for 2 hours at room temperature. Water (1 ml) was added and the solvent removed in vacuo. The residue was dissolved in ethyl acetate (50 ml) and washed with water (2×40 ml), followed by 1N hydrochloric acid (40 ml). The organic extract was dried over magnesium sulphate, filtered and preadsorbed onto silica. Purification by column chromatography on silica eluting with 70% ethyl acetate in heptane, followed by trituration with diethyl ether afforded the title compound as a white solid (170 mg).
TLC $R_f$ 0.63 (ethyl acetate).
Mass spectrum m/z 403 [M+H].

EXAMPLE 3

7-Methoxy-2-methoxymethylbenzofuran-4-carboxylic Acid (5cyano-3-methyl-3H-imidazol-4-yl)-amide Prepared from 7-methoxy-2-methoxymethylbenzofuran4-carboxylic acid 4-nitro-phenyl ester (250 mg) and 5-amino-1-methyl-1-H-imidazole-4-carbonitrile (171 mg). The reaction was stirrred for 1 hour and 40 minutes. Water (1 ml) was added and the solvent removed in vacuo. Purification by column chromatography on silica eluting with 10% methanol in dichloromethane afforded the title compound as a pale yellow solid (178 mg).
TLC $R_f$ 0.35 (10% methanol in dichloromethane).
Mass spectrum m/z 339[M−H]

EXAMPLE 4

7-Difluoromethoxy-2-methoxymethylbenzofuran-4carboxylic Acid (4-cyano-2-methyl-2-pyrazol-3-yl)-amide Prepared from 7-difluoromethoxy-2-methoxymethylbenzofuran-4-carboxylic acid 4-nitrophenyl ester (83 mg) and 5-amino-1-methyl-1-H-pyrazole-4-carbonitrile (52 mg) at 0° C. The reaction was stirred for 90 minutes at room temperature. Water (1 ml) was added and the solvent removed in vacuo. Purification by column chromatography on silica eluting with 70% ethyl acetate in heptane, followed by trituration with diethyl ether afforded the title compound (21 mg).
TLC $R_f$ 0.35 (70% ethyl acetate in heptane).
Mp 118–120° C.

EXAMPLE 5

7-Methoxy-2-(tetrahydrofuran-3-yl)-benzofuran-4-carboxylic Acid (4-cyano-2-methyl-2-pyrazol-3-yl)-amide Prepared from 7-methoxy-2-(tetrahydrofuran-3-yl)-benzofuran-4-carboxylic acid 4-nitrophenyl ester (200 mg) and 5-amino-1-methyl-1-H-pyrazole-4-carbonitrile (127 mg)at 0° C. The reaction was stirred for 60 minutes at room temperature. Water (1 ml) was added and the solvent removed in vacuo. Purification by column chromtography on silica eluting with 10% methanol in dichloromethane followed by gradient preparative HPLC on a Phenomenex LUNA(2)198 C18 column eluting with 0.05% trifluoroacetic acid in 20%–65% acetonitrile in water afforded the title compound (19 mg) as a white solid.
TLC $R_f$ 0.47 (ethyl acetate).
Mp 186–188.8° C.

EXAMPLE 6

7-Methoxy-2-(tetrahydrofuran-2-yl)-benzofuran-4-carboxylic Acid (4-cyano-2-methyl-2-pyrazol-3-yl)-amide Prepared from 7-methoxy-2-(tetrahydrofuran-2-yl)-benzofuran-4-carboxylic acid 4-nitrophenyl ester (370 mg) and 5-amino-1-methyl-1-H-pyrazole-4 carbonitrile (122 mg). The residue obtained from removing solvent in vacuo was dissolved in ethyl acetate (50 ml) and washed with water (50 ml) followed 1 N hydrochloric acid (25 ml). The organic extract was dried over magnesium sulphate, filtered and preadsorbed onto silica. Purification by column chromatography on silica eluting with ethyl acetate afforded the title compound as a white solid (166 mg).
TLC $R_f$ 0.56 (ethyl acetate).
Mp 114.5–116° C.

EXAMPLE 7

7-Methoxy-2-methoxymethylbenzofuran-4-carboxylicacid (4-cyano-2-methyl-2-pyrazol-3-yl)-amide Oxalyl chloride (0.07 ml) was added to a stirred solution of 7-methoxy-2-methoxymethylbenzofuran-4-carboxylic acid (100 mg) in dry dichloromethane (20 ml) at room temperature under a dry nitrogen atmosphere. N,N-dimethylformamide (catalytic amount) was added and the reaction allowed to stir overnight. The solvent was removed in vacuo to afford the corresponding acid chloride as an oily yellow solid.

To a stirred solution of 5-amino-1-methyl-1-H-pyrazole-4-carbonitrile (155 mg) in N,N-dimethylformamide (7 ml) under an atmosphere of nitrogen at 0° C. was added sodium hydride (51 mg, 60% dispersion in mineral oil). The reaction was stirred at 0° C. for 5 minutes. A solution of the acid chloride in N,N-dimethylformamide (8 ml) was added and the reaction stirred at room temperature for 2 hours. Water (1 ml) was added and the solvent removed in vacuo. Purification by column chromatography on silica eluting with 1% methanol in dichloromethane followed by trituration with 50% diethyl ether in hexane afforded the title compound as a pale yellow solid (4 mg).
TLC $R_f$ 0.52 (10% methanol in dichloromethane).
Mass spectrum m/z 339[M−H]

EXAMPLE 8

7-Difluoromethoxy-2-(tetrahydrofuran-3-yl)-benzofuran-4-carboxylic Acid (3,5-dimethylisoxazol-4-yl)-amide Oxalyl chloride (0.09ml) was added to a stirred solution of 7-difluoromethoxy-2-(tetrahydrofuran-3-yl)-benzofuran-4-carboxylic acid (0.15 g) in dry dichloromethane (20 ml) at room temperature under a dry nitrogen atmosphere. N,N-dimethylformamide (catalytic amount) was added and the reaction allowed to stir for 2 hours. The solvent was removed in vacuo to furnish the corresponding acid chloride as a yellow oil.

3,5-Dimethylisoxazol-4-ylamine (0.11 g) was added to a stirred solution of the acid chloride in dry dichloromethane (30 ml) at room temperature under a dry nitrogen atmosphere. Triethylamine (0.14 ml) was added and the reaction allowed to stir at room temperature for 2 hours. The reaction was washed with water (30 ml) and 1N hydrochloric acid (30 ml). The organic phase was dried over magnesium sulphate, filtered and preadsorbed onto silica. Purification by column chromatography on silica eluting with 30% heptane in ethyl acetate yielded the title compound as a white solid (0.16 g).
TLC $R_f$ 0.17 (50% ethyl acetate in heptane)
Mp 155.5–156.5° C.

The following compounds were prepared in a similar manner.

EXAMPLE 9

7-Methoxy-2-(tetrahydrofuran-2-yl)-benzofuran-4-carboxylic Acid (3,5-dimethylisoxazol-4-yl)-amide Starting from 7-methoxy-2-(tetrahydrofuran-2-yl)-benzofuran-4-carboxylic acid (262 mg) and 3,5-dimethylisoxazol-4-ylamine (120 mg). Purification by column chromatography on silica eluting with 30% ethyl acetate in hexane afforded the title compound as an off-white solid (238 mg).
TLC $R_f$ 0.36 (50% ethyl acetate in hexane)
Mass spectrum m/z 357 [M+H].

EXAMPLE 10

7-Methoxy-2-methoxymethylbenzofuran-4-carboxylic Acid (3,5-dimethylisoxazol-4-yl)-amide Starting from 7-methoxy-2-methoxymethylbenzofuran-4-carboxylic acid (0.19 g) and 3,5-dimethylisoxazol-4-ylamine (88 mg). Purification by column chromatography on silica eluting with ethyl acetate afforded the title compound as a cream solid (0.18 g).
TLC $R_f$ 0.17 (5% methanol in dichloromethane)
Mp 168.5–169.5° C.

EXAMPLE 11

7-Methoxy-2-methoxymethylbenzofuran-4-carboxylic Acid (4-chloro-2-methyl-2H-pyrazol-3-yl)-amide Starting from 7-methoxy-2-methoxymethylbenzofuran-4-carboxylic acid (0.14 g) and 4-chloro-2-methyl-2H-pyrazol-3-ylamine (78 mg). Purification by column chromatography on silica eluting with 50%–75% ethyl acetate in hexane afforded the title compound as an off white solid (34 mg).
TLC $R_f$ 0.57 (ethyl acetate)
Mp 158–160° C.

EXAMPLE 12

7-Methoxy-2-methoxymethylbenzofuran-4-carboxylic Acid (2-methyl-2H-pyrazol-3-yl)-amide Starting from 7-methoxy-2-methoxymethylbenzofuran-4-carboxylic acid (93 mg) and 2-methyl-2H-pyrazol-3-ylamine (40 mg). Purification by column chromatography on silica eluting with ethyl acetate afforded the title compound as a white solid (43 mg).
TLC $R_f$ 0.4 (ethyl acetate).
Mp 148–150° C.

EXAMPLE 13

7-Methoxy-2-methoxymethylbenzofuran-4-carboxylic Acid (2-ethyl-2H-pyrazol-3-yl)-amide Starting from 7-methoxy-2-methoxymethylbenzofuran-4-carboxylic acid (0.15 g) and 2-ethyl-2H-pyrazol-3-ylamine (85 mg). Purification by column chromatography on silica eluting with 50% ethyl acetate in heptane increasing to ethyl acetate afforded the title compound as a yellow solid (35 mg).
TLC $R_f$ 0.35 (ethyl acetate)
Mp 97–99° C.

EXAMPLE 14

7-Methoxy-2-methoxymethylbenzofuran-4-carboxylic Acid (2,4-dimethyl-2H-pyrazol-3-yl)-amide Starting from 7-methoxy-2-methoxymethylbenzofuran4-carboxylic acid (0.1 g) and 2,4-dimethyl-2H-pyrazol-3-ylamine (56 mg). Purification by column chromatography on silica eluting with 20% heptane in ethyl acetate and gradient preparative HPLC on a PhenomenexLUNA(2)™ C18 column eluting with 0.05% trifluoroacetic acid in20%–65% acetonitrile in water gave the title compound as a pale yellow solid (39 mg).
TLC $R_f$ 0.33 (ethyl acetate)
Mass spectrum m/z 328 [M−H].

EXAMPLE 15

7-Difluoromethoxy-2-methoxymethylbenzofuran-4-carboxylic Acid (3,5-dimethylisoxazol-4-yl)-amide Cyanuric chloride (19 mg) and triethylamine (0.05 ml) were added to a stirred solution of 7-difluoromethoxy-2- methoxymethylbenzofuran-4-carboxylic acid (85 mg) in dry dichloromethane at room temperature under a dry nitrogen atmosphere. After stirring for 20 minutes 3,5-dimethylisoxazol-4-ylamine (42 mg) was added and the reaction left overnight. The reaction was mixture was preadsorbed onto silica. Purification by column chromatography on silica eluting with 30% ethyl acetate in hexane gave the title compound as a cream solid (33 mg)

TLC $R_f$ 0.52 (50% ethyl acetate in hexane)

Mass spectrum m/z 367 [M+H].

We claim:

1. A method for the treatment of a disease state selected from the group consisting of Crohn's disease and multiple sclerosis, said method comprising administering to a person or animal an effective amount of a compound of the formula

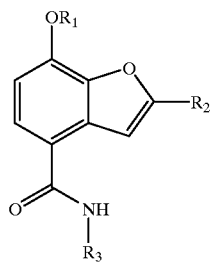

wherein $R_1$ is $C_{1-3}$ alkyl optionally substituted with one or more fluorines;

$R_2$ is $CH_2OCH_3$ or 2 or 3-tetrahydrofuranyl;

$R_3$ is a pyrazole, imidazole or isoxazole group of partial formula (A), (B) or (C)

(A)

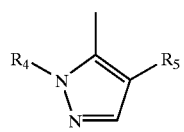

(B)

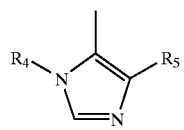

(C)

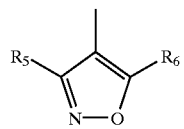

$R_4$ is $C_{1-3}$ alkyl; and $R_5$ and $R_6$, which may be the same or different, each represents $C_{1-3}$ alkyl, halogen, $CF_3$ or CN;

or a pharmaceutically-acceptable salt thereof.

2. A method for the treatment of a disease state selected from the group consisting of HIV infection, AIDS, ARC, and systemic lupus erythematosus, said method comprising administering to a person or animal an effective amount of a compound of the formula

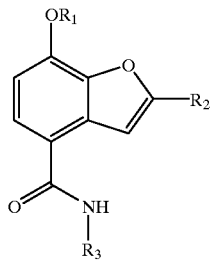

wherein $R_1$ is $C_{1-3}$ alkyl optionally substituted with one or more fluorines;

$R_2$ is $CH_2OCH_3$ or 2 or 3-tetrahydrofuranyl;

$R_3$ is a pyrazole, imidazole or isoxazole group of partial formula (A), (B) or (C)

(A)

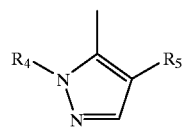

(B)

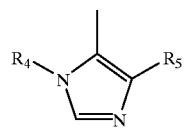

(C)

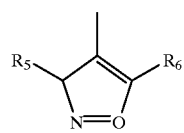

$R_4$ is $C_{1-3}$ alkyl; and $R_5$ and $R_6$, which may be the same or different, each represents $C_{1-3}$ alkyl, halogen, $CF_3$ or CN;

or a pharmaceutically-acceptable salt thereof.

3. The method according to claim 1, wherein the disease state is Crohn's disease.

4. The method according to claim 1, wherein the disease state is multiple sclerosis.

5. The method according to claim 2, wherein the disease state is HIV infection.

6. The method according to claim 2, wherein the disease state is AIDS.

7. The method according to claim 2, wherein the disease state is ARC.

8. The method according to claim 2, wherein the disease state is systemic lupus erythematosus.

* * * * *

UNITED STATES PATENT AND TRADEMARK OFFICE
CERTIFICATE OF CORRECTION

PATENT NO. : 6,455,561 B1  Page 1 of 1
DATED : September 24, 2002
INVENTOR(S) : Hazel Joan Dyke, Christopher Lowe and John Gary Montana It is certified that error appears in the above-identified patent and that said Letters Patent is hereby corrected as shown below:

Column 20,
Lines 35-40, " 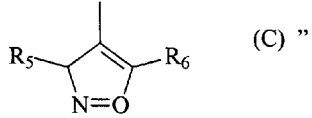 (C) "

should read

-- 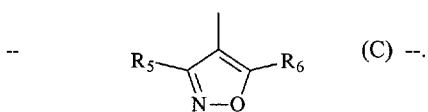 (C) --.

Signed and Sealed this

Eleventh Day of March, 2003

JAMES E. ROGAN
*Director of the United States Patent and Trademark Office*